United States Patent [19]
Klose

[11] Patent Number: 6,013,286
[45] Date of Patent: *Jan. 11, 2000

[54] ENCAPSULATED BIOACTIVE SUBSTANCES

[75] Inventor: Robert E. Klose, West Nyack, N.Y.

[73] Assignee: Balchem Corporation, Slate Hill, N.Y.

[*] Notice: This patent is subject to a terminal disclaimer.

[21] Appl. No.: 07/987,211

[22] Filed: Dec. 8, 1992

Related U.S. Application Data

[63] Continuation of application No. 07/706,859, May 29, 1991, Pat. No. 5,190,775.

[51] Int. Cl.$^7$ .................................................. A23K 1/16
[52] U.S. Cl. ................................ 426/2; 426/98; 426/635
[58] Field of Search ...................................... 424/463, 498; 426/2, 96, 97, 98, 72, 73, 74, 303, 307, 635

[56] References Cited

U.S. PATENT DOCUMENTS

| | | |
|---|---|---|
| 2,560,830 | 7/1951 | Turner . |
| 2,581,038 | 1/1952 | Middendorf . |
| 2,648,609 | 8/1953 | Wurster . |
| 2,799,241 | 7/1957 | Wurster . |
| 2,970,911 | 2/1961 | Lorz . |
| 3,015,128 | 1/1962 | Somerville, Jr. . |
| 3,110,626 | 11/1963 | Larson et al. . |
| 3,159,874 | 12/1964 | Langer et al. . |
| 3,163,579 | 12/1964 | Derivan . |
| 3,279,994 | 10/1966 | Koff . |
| 3,341,466 | 9/1967 | Brynko et al. . |
| 3,356,569 | 12/1967 | Nicodemus . |
| 3,436,223 | 4/1969 | Wehrmeister . |
| 3,471,304 | 10/1969 | Hamdy et al. . |
| 3,475,177 | 10/1969 | Jones . |
| 3,541,204 | 11/1970 | Sibbald et al. . |
| 3,819,838 | 6/1974 | Smith et al. . |
| 3,959,493 | 5/1976 | Baalsrud et al. . |
| 4,086,365 | 4/1978 | Snetsinger et al. . |
| 4,196,187 | 4/1980 | Dannelly et al. . |
| 4,497,845 | 2/1985 | Percel et al. . |
| 4,511,584 | 4/1985 | Percel et al. . |
| 4,537,784 | 8/1985 | Percel et al. . |
| 4,542,031 | 9/1985 | Nakajima et al. . |
| 4,595,584 | 6/1986 | Wu et al. . |
| 4,687,676 | 8/1987 | Wu et al. . |
| 4,713,245 | 12/1987 | Ando et al. . |
| 4,717,567 | 1/1988 | Wu et al. . |
| 4,772,477 | 9/1988 | Weiss et al. . |
| 4,775,540 | 10/1988 | Hertel et al. . |
| 4,797,288 | 1/1989 | Sharma et al. . |
| 4,832,967 | 5/1989 | Autant et al. . |
| 4,837,004 | 6/1989 | Wu et al. . |
| 4,842,863 | 6/1989 | Nishimura et al. . |
| 4,876,097 | 10/1989 | Autant et al. . |
| 4,948,589 | 8/1990 | Iijima et al. ............................ 424/438 |
| 4,960,600 | 10/1990 | Kester et al. . |
| 4,971,804 | 11/1990 | Ghebre-Sellassie .................... 424/490 |
| 5,190,775 | 3/1993 | Klose .......................................... 426/2 |

FOREIGN PATENT DOCUMENTS

| | | |
|---|---|---|
| 760193 | 10/1956 | United Kingdom . |
| 765885 | 1/1957 | United Kingdom . |
| 936386 | 9/1963 | United Kingdom . |
| 972128 | 10/1964 | United Kingdom . |

OTHER PUBLICATIONS

Hawley "The Condensed Chemical Dictionary" Van Nostrand Reinhold Co., 10th Edition, pp. 246, 450, 546, 929–930, 961, 968, and 1095.

*Primary Examiner*—Curtis E Sherrer
*Attorney, Agent, or Firm*—Banner & Witcoff, Ltd.

[57] ABSTRACT

A composition of matter and method for administering a bioactive substance to the post-rumen portion of the digestive system of a ruminant substantially without introducing the substance to the rumen portion of the digestive system is provided. The composition of matter comprises particles which have a specific gravity between about 0.3 and 2.0, preferably between about 1.0 and 2.0. The particles comprises a core comprising bioactive substance; a hydrophobic coating essentially completely encapsulating said core in a quantity sufficient to essentially preclude introduction of bioactive substance into the rumen; and a surfactant applied to the surface of the hydraphobic coating in a quantity sufficient to ensure that said particles do not float on the rumen. The method comprises orally administering this composition of matter to a ruminant.

17 Claims, No Drawings

ENCAPSULATED BIOACTIVE SUBSTANCES

This application is a continuation of application Ser. No. 07/706,859, filed on May 29, 1991, now U.S. Pat. No. 5,190,775.

TECHNICAL FIELD

This invention relates to a method for providing bioactive substances, preferably choline chloride, to a ruminant in a form which is capable of substantially preventing release of the substance in the rumen.

BACKGROUND OF THE INVENTION

It has been widely established that very significant increases in animal feeding efficiencies can be obtained by the use of certain feed additives. This has been particularly true in the feeding of monogastrics where it is now the usual practice to supplement the diet with such materials as amino acids. The amino acids represent a particularly useful group of additives since they are the units from which protein molecules are constructed. Although many biologically active materials are employed as feed additives, it is recognized that many of these are inefficiently utilized by ruminants due to degradation thereof in the rumen. Thus, materials such as amino acids and vitamins are not used routinely in ruminant feeds because of their susceptibility to ruminal degradation.

The rumen, which is essentially a continuous fermenter, supports a variety of micro-organisms under neutral conditions (pH=5–8) which attack and digest much of the feed as part of their normal life cycle. The rumen micro-organisms use the feed to synthesize microbial protein. A stream of ingesta, rich in microbial cells, passes out of the rumen into the omasum. The function of the omasum is to separate liquids and solids. Much of the liquid reenters the rumen while the remainder of the material enters the abomasum or true stomach. Digestion and absorption then proceed in the abomasum in a manner similar to that found in monogastrics. Enzymes secreted into the lumen of the abomasum digest much of the material, including some of that contained in the microbial cells.

The rumen has the great advantage of being able to convert by microbial action many feed components which have no direct nutritive value for the host into products which can be assimilated and utilized by the host. For example, urea may be converted to microbial protein which subsequently may be digested and utilized by the host animal. Cellulose may be converted to a mixture of volatile fatty acids which can serve as a source of energy to the host.

Unfortunately, this microbial action also presents certain disadvantages. For instance, soluble proteins of high nutritive value may be digested and deaminated in the rumen and in part resynthesized into microbial protein of lower nutritive value. Amino acids, the units from which protein molecules are constructed, are also chemically changed by the rumen microorganisms which convert amino acids to carbon dioxide, volatile fatty acids, and ammonia.

It is well recognized in the art that this microbial activity of the rumen limits the productivity of ruminants. Consequently, a great deal of effort has been expended towards providing a bioactive substance in a form which will pass through the rumen essentially unaltered, yet undergo disintegration and absorption in the abomasum.

Numerous patents disclose coating bioactive substances with material which survives the rumen but degrades in the abomasum. For example, Ando U.S. Pat. No. 4,713,245 discloses a rumen-surviving granule comprising a core of bioactive material, a coating substance stable at neutral pH (as found in the rumen) but dissolved or disintegrated at pH=3 (as found in the abomasum), and at least one other coating selected from the group consisting of fatty acids having at least 14 carbon atoms and waxes, animal fat, and vegetable fat having a melting point of 40° C. or higher.

Autant U.S. Pat. No. 4,832,967 discloses a two-layer rumensurviving coating for water-soluble bioactive substances. The resulting particulate is stable at pH at least as high as 5.5, and releases bioactive substance at pH of 3.5 or less. The coating medium comprises a first coating layer consisting of material sensitive to pH variations and a second coating layer consisting of a hydrophobic composition which must include inorganic filler if the bioactive core has not undergone a surface treatment (application of hydrophobic binder). This hydrophobic outer coating layer is provided with a texture which permits diffusion or penetration of the external liquid medium. The outer coating preferably contains a mixture of hydrophobic substances.

Autant U.S. Pat. No. 4,876,097 discloses a coating composition which is stable at pH less than or equal to about 3.5. The coating comprises a film-forming, water-insoluble binder which contains a substance which controls hydrophilicity, and optionally a substance which is sensitive to pH. Both waxes (hydrophobic) and propylene glycol (water-soluble) are suitable for controlling the hydrophilic/hydrophobic balance. Controlling the hydrophilicity of the particle is said to limit release of the bioactive material in neutral or slightly acidic media, i.e., in the rumen. In very acidic media, i.e., the abomasum, pH-sensitive fillers are activated by the media, which diffuses slowly at a rate established by the hydrophilicity of the coating. The resulting dissolution or swelling of the pH-sensitive filler degrades the coating and releases the bioactive material.

Sibbald U.S. Pat. No. 3,541,204 discloses hydrogenated vegetable and animal fats and waxes such as rice bran wax as coatings which survive the rumen but are disrupted in the intestinal tract.

One well recognized problem with such coatings that can survive the environment of the rumen is that the coated granules tend to float on the contents of the rumen. If the capsules or granules float for a sufficient period, they will be regurgitated. Regurgitation increases the likelihood that the coating will be compromised or destroyed during rumination. Consequently, many of the above described patents provide for adjustment of the density of the capsule or granule by addition of a high density weighting agent, to ensure that the granule sinks. However, as disclosed by Sibbald, the density must not be so great that the capsule will sink to the floor of the rumen and remain there indefinitely. Sibbald discloses an adjusted density of 0.8 to 2.0, preferably about 1.0 to 1.4, g/cc.

However, the art has not recognized that particles coated with hydrophobic material will float on water (and on rumen), even though the particles have been densified to a specific gravity greater than that of water (or rumen). Rather, the art teaches that densification alone provides the proper particle/fluid interaction and precludes undersirable flotation of particles.

SUMMARY OF THE INVENTION

The present invention is directed to a composition of matter comprising particles suitable for introduction of a bioactive substance to the post-rumen portion of the digestive system of a ruminant substantially without introducing said substance to the rumen portion of the digestive system. The particles have a specific gravity between about 0.3 and 2.0, preferably between about 1.0 and 2.0. The particles comprise a core comprising bioactive substance; a hydrophobic coating essentially completely encapsulating said core in a quantity sufficient to essentially preclude introduction of bioactive substance into the rumen; and a surfactant applied to the surface of the hydrophobic coating in a quantity sufficient to ensure that said particles do not float on the rumen.

The present invention also provides a method for administering a bioactive substance to the post-rumen portion of the digestive system of a ruminant substantially without introducing the substance to the rumen portion of the digestive system. The method comprises orally administering a composition of matter comprising a core comprising bioactive substance; a hydrophobic coating essentially completely encapsulating said core in a quantity sufficient to essentially preclude introduction of bioactive substance into the rumen; and a surfactant applied to the surface of the hydrophobic coating in a quantity sufficient to ensure that said particles do not float on the rumen.

DETAILED DESCRIPTION OF THE INVENTION

It has been discovered that a bioactive substance that has been coated with a hydrophobic coating to prevent premature release in the rumen, will more effectively pass through the rumen, if a surface active agent is applied to the surface of the hydrophobic coating.

The term bioactive substance used herein includes nutrients and drugs. Examples of such substances includes amino acids, amino acid derivatives, proteins, vitamins, enzymes, carbohydrates, drugs, hormones, etc. Examples of amino acids include: methionine, lysine, threonine, leucine, isoleucine, tryptophan, phenylalanine, valine and glycine. Examples of amino acid derivatives include: N-acylamino acids, e.g., N-stearoylmethionine, N-oleoylmethionine, the calcium salt of N-hydroxymethylmethionine, lysine hydrochloride, methionine hydroxy analogues and sodium glutamate. Examples of proteins include: feather meal, fish meal, casein, corn protein and potato protein. Examples of vitamins include: vitamin A, vitamin A palmitate, vitamin A acetate, beta-carotene, vitamin $D_2$, vitamin $D_3$, vitamin E, menadion sodium bisulfite, the B vitamins, e.g., thiamine, thiamine hydrochloride, riboflavin, nicotinic acid, nicotinic acid amide, calcium pantothenate, choline pantothenate, pyridoxine hydrochloride, choline chloride, cyanocobalamin, biotin, folic acid and p-aminobenzoic acid. Examples of enzymes include: protease preparation, amylase preparation, mixed enzyme preparation and lipase preparation. Examples of carbohydrates include starch, glucose, and sucrose. Examples of drugs for animal use include: antibiotics such as tetracyclines, aminoglycosides, macrolides, polypeptides, polysaccharides and polyethers, vermifuges such as Negphone, and antiparasitics such as piperazine salts. Examples of hormones include: estrous hormones such as estrogen, stilbestrol and hexestrol, and thyroid hormones such as thyroprotein and goitrogen.

Although these substances are generally used alone, they may also be used in combination as a mixture.

In accordance with the present invention, particles or granules of such bioactive substances are encapsulated in a hydrophobic coating. The hydrophobic coating prevents release of the bioactive substances into the rumen portion of the digestive system, and allows release of the bioactive substances posterior to the omasum. The coating must be essentially insoluble and impermeable in the rumen. As disclosed by the above-described prior art, the coating therefore must be stable at essentially neutral pHs (i.e. stable in a pH range from about 5.5 to about 8), and must have a melting point higher than the temperature of the rumen fluid (e.g., about 40° C.). Furthermore, because it is desired to release the bioactive substance in the digestive tract posterior to the omasum, the coating must dissolve or become permeable only in the abomasum or subsequent intestinal tract. Such a coating may be dissolved or disintegrated at a pH of about 3.5 or less; alternatively, the coating may be attacked by bile salts or enzymes or by a combination of these factors.

Any hydrophobic coating, or mixture thereof, which meets the above described requirements can be used in this invention. Preferred coatings comprise hydrogenated vegetable oils including triglycerides such as hydrogenated cottonseed, corn, peanut, soybean, palm, palm kernel, babassu, sunflower and safflower oils. Preferred hydrogenated vegetable oils include hydrogenated palm oil, cottonseed oil and soybean oil. The most preferred hydrogenated vegetable oil is hydrogenated soybean oil. Other vegetable- and animal-derived fats and waxes also are suitable. Other ingredients which can be incorporated in the hydrophobic coating include beeswax, petroleum wax, and lower melting hydrogenated vegetable oil blends. Other waxes and oils such as rice bran wax and castor wax also are suitable components in the hydrophobic coating of the present invention.

The method of applying the coating to the granule is not critical, forms no part of the present invention, and may be performed in any manner. For instance, the granules may be suspended in the liquid coating and the suspension sprayed into a "freezing chamber." Alternatively, the granules may be sprayed with the coatings of the present invention, the granules being suspended by a flow of air (fluidized bed). U.S. Pat. No. 4,511,584 at columns 3–5 and U.S. Pat. No. 4,511,592 at column 4, the disclosures of which are incorporated herein by reference, teach preferred methods of applying fat coatings to granular particles. U.S. Pat. No. 4,537,784 at columns 3–4; U.S. Pat. No. 4,497,845 at column U.S. Pat. Nos. 4; 3,819,838; 3,341,466; 3,279,994; 3,159,874; 3,110,626; 3,015,128; 2,799,241; and 2,648,609, which disclosures are all incorporated herein by reference, teach additional methods and apparatus for applying coatings which may be used to produce the coated granules used in the present invention.

This invention is particularly useful for delivering the bioactive substance choline chloride to ruminants; however, the invention is in no way limited to choline chloride as the bioactive substance. When choline chloride is used, 70 percent choline chloride on a cereal carrier is the preferred form. One method of preparing 70 percent choline chloride on a cereal carrier is addition of an aqueous solution of choline chloride (for example, 70 percent choline chloride in water) to commercially available dry 60 percent choline chloride on a cereal carrier, then drying the particles.

It has surprisingly been discovered that the hydrophobic coating is more effective at preventing the premature release of choline chloride when applied to 70 percent choline chloride on a cereal carrier as opposed to 60 percent choline chloride on a cereal carrier.

The hydrophobic coating is typically applied in the range from about 10 to about 80 percent by weight, preferably about 40 to about 60 percent by weight based on the total weight of the encapsulate. The bioactive substance plus the dry cereal carrier is typically in the range from about 20 to 90 percent by weight, preferably about 40 to about 60 percent by weight based on the total weight of the encapsulate. The bioactive substance plus dry cereal carrier is typically about 60 percent choline chloride by weight to about 70 percent choline chloride, by weight, preferably about 70 percent choline chloride by weight.

While densification of the capsules is not essential to the practice of the invention, it is desirable to adjust the density of the capsules to prevent flotation thereof on the contents of the rumen. Such densification must be done carefully to avoid causing densified particles to sink to the bottom of the rumen to minimize both destruction of the coating through rumination and the residence time in the rumen. Accordingly, a high density additive such as kaolin or particulate iron is incorporated in the capsules to yield the desired density. The capsules are typically weighted to a specific gravity range of about 1 to about 2, preferably at least about 1.35, more preferably to about 1.4. The high density additives can be added at any time prior to or during the coating process. The preferred density modifier is iron, typically added in the range of about 0 to about 25 percent by weight, preferably about 10 to about 15 percent by weight of the coated densified product.

It has surprisingly been discovered that even with densification of the capsules as described above, capsules will still float on water and presumably on the contents of the rumen. While not wanting to be bound by theory, it is believed that such coated and densified capsules float because of the hydrophobic nature of the coating. It has further been discovered that this tendency of the densified capsules to float can be overcome by treating the capsules with a surfactant or wetting agent. It has surprisingly been discovered that treatment of encapsulated bioactive substances with a wetting agent in accordance with the present invention not only promotes sinking of densified (specific gravity greater than about 1.0) capsules, but also promotes sinking of un-densified capsules (specific gravity below about 1.0). Accordingly, the present invention encompasses capsules with specific gravities in the range from about 0.3 to about 2.0, preferably in the range of about 0.8 to about 2.0, most preferably in the range from about 1.35 to about 1.5.

Suitable wetting agents include, for example, polysorbate 60, polysorbate 80, propylene glycol, sodium dioctylsulfosuccinate, and combinations thereof. Other surface active agents, wetting agents, and emulsifiers such as, but not limited to, sodium lauryl sulfate, lactylic esters of fatty acids, polyglycerol esters of fatty acids, triacetin, and lecithin, are also suitable for use in this invention. The wetting agents are typically added in the range of about 0.01 to about 10 percent by weight, preferably in the range of about 0.1 to about 3.0 percent by weight for polysorbate 60, polysorbate 80, and sodium dioctylsulfosuccinate, and preferably about 1 to about 5 percent by weight for propylene glycol.

The wetting agent can be applied to the capsules by any convenient method. Preferably, the wetting agent is applied by spraying. The wetting agent can be applied immediately after encapsulation, while the coating is still warm, or after the capsules have cooled. Preferably, the wetting agent is applied after the capsules have cooled.

Skilled practitioners recognize that flow agents, such as finely-divided silica, can be admixed with the particles of the invention to facilitate handling.

The following examples are for illustrative purposes only and are not meant to limit the claimed invention in any manner.

EXAMPLES

| Composition of Encapsulate | Wt. % |
| --- | --- |
| Bioactive Substrate 70 percent Choline Chloride on cereal carrier | 47.2 |
| Hydrophobic Coating | 37.8 |
| Density Modifier Reduced Iron | 15.0 |

The coating components were melted and mixed together. The substrate was coated by spraying the encapsulate thereon. The iron density modifier was added during the coating process after approximately one-half of the coating was applied. After cooling, the encapsulated product was passed through a six mesh screen to break-up agglomerates. In all examples, the resulting product had a specific gravity of about 1.4.

In all of Examples 1 through 13, the treated and untreated encapsulates were tested to determine whether they would float on water. In every case, even though the encapsulate specific gravity was much greater than that of water (1.4 vs. 1.0), the untreated encapsulate floated on the water. However, in every case, the treated encapsulate sank immediately.

Example 1

The hydrophobic coating was a mixture of approximately 90 percent partially hydrogenated soybean oil and 10 percent beeswax. A portion of the resulting encapsulate was treated with the wetting agent UNIWET DOSS-75 sodium dioctysulfosuccinate by spraying the wetting agent onto the encapsulate in a ratio of about 2.5 ounces of UNIWET to about ten pounds of encapsulate.

Example 2

The hydrophobic coating for Example 2 was the same as that used in Example 1. A portion of the encapsulate was treated by spraying propylene glycol wetting agent on to the encapsulate in a ratio of about 15 gm propylene glycol to about 500 gm of encapsulate.

Example 3

The hydrophobic coating was 100 percent partially hydrogenated soybean oil. A portion of the encapsulate was treated with propylene glycol as the wetting agent in the same manner as in Example 2.

Example 4

The hydrophobic coating was a mixture of 90 percent partially hydrogenated soybean oil and 10 percent of a partially hydrogenated blend of soybean and cottonseed oil. A portion of the encapsulate was treated with propylene glycol as the wetting agent in the same manner as in Example 2.

Example 5

The hydrophobic coating for Example 5 was the same as that used in Example 4. A portion of the encapsulate was treated with polysorbate 60 wetting agent at a ratio of about 2.5 gm polysorbate 60 to about 250 gm of encapsulate. Finally, 1 wt percent of micron-sized silica was added as a flow agent.

Example 6

The hydrophobic coating of Example 6 was the same as that of Example 4. A portion of the encapsulate was treated with polysorbate 80 wetting agent at a concentration of about 0.4 wt percent of the encapsulate.

Example 7

The hydrophobic coating of Example 7 was the same as that of Example 4. A portion of the encapsulate was treated with the wetting agent polysorbate 80 at a concentration of about 0.2 percent of the encapsulate.

Examples 8 through 11

The hydrophobic coating of Examples 8 through 11 was the same as that of Example 4. For each of Examples 8, 9, 10, and 11, the wetting agent UNIWET DOSS-75 was applied at concentrations of 1.0 percent, 0.5 percent, 0.25 percent, and 0.125 percent of the encapsulate, respectively.

Example 12

The hydrophobic coating for Example 12 was the same as that used in Example 1. Encapsulate (299.4 grams) was treated with 0.6 grams of triacetin (Kodaflex Triacetin Plasticizer 4X 900 928) as the wetting agent.

Example 13

The hydrophobic coating for Example 13 was the same as that used in Example 1. Encapsulate (299.4 grams) was treated with 0.6 grams of the lecithin (Van den Bergh DUR-LEC B #12959) as the wetting agent.

Example 14

For Example 14 the following composition was used:

| Composition of Encapsulate | % | Weight lbs. | oz. |
| --- | --- | --- | --- |
| Bioactive Substrate 70 percent Choline Chloride on cereal carrier | 46.8 | 11 | 5.0 |
| Hydrophobic Coating 90 percent Partially Hydrogenated Soybean Oil 10 percent Partially Hydrogenated Blend of Soybean and Cottonseed Oils | 37.5 | 9 | 5.0 |
| Density Modifier Reduced Iron | 15.0 | 3 | 10.0 |
| Wetting Agent Polysorbate 80 | 0.2 | — | 0.75 |
| Flow Agent Micron-Sized Silica | 0.5 | — | 1.90 |

The coating components were melted together and applied to the substrate by spraying. The iron density modifier was added during the coating process after approximately one-half of the coating was applied. After application of the coating was complete, a portion of the encapsulated product (specific gravity about 1.4) was treated with the wetting agent. The encapsulated treated product then was mixed with the flow agent.

Both treated and untreated encapsulates of Example 14 were tested to determine whether they would float on water. Even though the encapsulate specific gravity (1.4) was much greater than that of water (1.0), the untreated encapsulates floated. However, the treated encapsulates sank immediately.

Example 15

The same formulation and method of preparation as used in Example 14, except the wetting agent was 3.5 oz. of polysorbate 60 and no flow agent was added.

As in Example 14, both treated and untreated encapsulates were tested to determine whether they would float on water. Even though the encapsulate specific gravity (1.4) was much greater than that of water (1.0), the untreated encapsulate floated. However, the treated encapsulate sank immediately.

Example 16

For Example 16 the following composition was used:

| Composition of Encapsulate | % | Weight lbs. | oz. |
| --- | --- | --- | --- |
| Bioactive Substrate 70 percent Choline Chloride on cereal carrier | 70 | 15 | 0 |
| Hydrophobic Coating Partially Hydrogenated Soybean Oil | 30 | | |

The coating material was melted and applied to the substrate by spraying. No density modifier was added. After cooling, 300 grams of the encapsulate was treated with 0.6 grams of polysorbate 80 wetting agent. The treated encapsulate was mixed with 1.5 grams of micron-sized silica. The resulting encapsulate had a specific gravity of approximately 0.6.

The treated and untreated encapsulates were tested to determine whether they would float on water. As expected, the untreated encapsulate, having a specific gravity (0.6) much less than that of water (1.0), floated. However, the treated encapsulate sank immediately, even though its specific gravity was much less than that of water.

Examples 17–27

The formulations for Examples 17 through 27 are set forth in Table I. For each of these examples the coating comprised a mixture of 90 percent partially hydrogenated soybean oil and 10 percent microcrystalline wax (unless otherwise indicated), and the density modifier was reduced iron. The coating was prepared by melting and mixing the components together. The resulting coating was applied to the dry substrate by spraying. Table I also sets forth the results from a 1 Hour Release Test, which represents the effectiveness of the encapsulate. The commercially available 60 percent choline chloride on a cereal carrier used in these examples was purchased from Ducon.

The 1 Hr Release Test results were obtained by the following procedure:

1. Place 1.0 gms. of encapsulate (to the nearest 0.1 mg) in a 250 ml. Erlenmeyer Flask. Add 100 ml. of distilled H$_2$O, then stopper flask.
2. Place the flask on a shaker and shake for 1 hour at moderate intensity.
3. At the end of 1 hour, filter the flask contents through premoistened glass wool into a second flask. Rinse the first flask with 5 ml. of water and powder funnel.

4. Add 1–2 ml. of 5 percent potassium chromate solution and titrate silver nitrate to the first permanent appearance of a buff color (due to silver chromate).

CALCULATION $$\text{percent Release} = \frac{(ml\,0.1\,N\,AgNO3)(139.63)(100)}{(mg\,sample)\frac{(\%\,Chol\,Chlor\,in\,Encap)}{100}}$$

Example 17

A 70 percent dry choline chloride substrate was prepared in the laboratory by adding an aqueous solution of 70 percent choline chloride to commercially available 60 percent dry choline chloride, followed by drying at room temperature. The iron density modifier was added after the coating process was partially completed.

Example 18

A 70 percent dry choline chloride substrate was prepared in the laboratory by adding an aqueous solution of 70 percent choline chloride to commercially available 60 percent dry choline chloride, followed by drying at room temperature. The iron density modifier was added to the substrate before drying and coating.

Example 19

The 70 percent dry choline chloride substrate was prepared in the laboratory by adding an aqueous solution of 70 percent choline chloride to commercially available 60 percent dry choline chloride, followed by oven drying at about 125° F. The iron density modifier was added after the coating process was partially completed. The coating comprised 10 percent beeswax in place of 10 percent microcrystalline wax.

Example 20

Example 20 was prepared by coating commercially available 60 percent choline chloride on a cereal carrier.

As can be seen in Table I, Example 20 released significantly more choline chloride during a 1 hour release test than did any of Examples 17, 18, or 19. Examples 17 through 20 therefore demonstrate the surprising and unexpected discovery that the hydrophobic coating was more effective at preventing the premature release of choline chloride when a 70 percent choline chloride on a cereal carrier substrate was used as opposed to a 60 percent choline chloride on a cereal carrier substrate.

Examples 21–27

Seventy percent choline chloride on a cereal carrier substrate was prepared in commercial-sized equipment. This 'commercially'-prepared 70 percent choline chloride substrate was used in Examples 21 through 24, 26, and 27. Standard 60 percent choline chloride sub strate was used for Example 25.

Example 21

The 'commercially'-prepared substrate described above was coated and densified with the same procedure and coating used in Example 19. As indicated by the 1 hour release test results, this substrate provided the same improved hydrophobic coating performance as the 70 percent choline chloride substrate prepared in the laboratory.

Example 22, 23, and 24

For Examples 22, 23, and 24, the iron density modifier was added after the coating process was partially completed, to a concentration of 15 percent. The coatings were 90 percent partially hydrogenated soy bean oil and 10 percent beeswax for Example 22, 100 percent partially hydrogenated soybean oil for Example 23, and 90 percent partially hydrogenated soybean oil and 10 percent of a mixture of partially hydrogenated cottonseed and soybean oils for Example 24. The 1 hour release test results for Examples 22, 23, and 24 demonstrate that good encapsulations can be achieved both at higher iron levels and with varying coating compositions.

Examples 25, 26, and 27

The coating for each of Examples 25, 26, and 27 was 100 per cent partially hydrogenated soybean oil. As can be seen in Table I, the 70 percent choline chloride substrate yields a more effective encapsulate (as demonstrated by the 1 hour release test) than the 60 percent choline chloride substrate, even when the encapsulates are not densified.

Examples 28–34

Table II displays the results of four laboratory preparations (Examples 28–31) of 70 percent choline chloride substrate from 60 percent choline chloride substrate and 70 percent aqueous choline chloride solution.

Table III displays the results of three laboratory preparations (Examples 32–34) of 75, 77.5, and 80 percent choline chloride substrates from 70 percent choline chloride substrate and 70 percent aqueous choline chloride solution.

The choline chloride analyses for both Tables II and III were performed by dissolving the sample in boiling water, adding 5 percent potassium chromate solution, and titrating while hot with standard silver nitrate solution.

Numerous characteristics and advantages of our invention have been set forth in the foregoing description, together with details of the structure and function of the invention, and the novel features thereof are pointed out in the appended claims. The disclosure, however, is illustrative only, and changes may be made in detail, especialy in matters of shape size, and arrangement of parts, within the principle of the invention, to the full extent indicated by the broad general meaning of the terms in which the appended claims are expressed.

TABLE I

Composition of Examples 17 to 27

| Example | 17 | 18 | 19 | 20 | 21 | 22 | 23 | 24 | 25 | 26 | 27 |
|---|---|---|---|---|---|---|---|---|---|---|---|
| Dry Substrate Composition, percent Choline Chloride on cereal carrier | 70 | 70 | 70 | 60 | 70 | 70 | 70 | 70 | 60 | 70 | 70 |
| Composition of Encapsulate | | | | | | | | | | | |
| Substrate (Wt. percent) | 50 | 50 | 48 | 50 | 48 | 47 | 47 | 47 | 70 | 70 | 80 |
| Coating (Wt. percent) | 40 | 40 | 39 | 40 | 39 | 38 | 38 | 38 | 30 | 30 | 20 |
| Density Modifier (Iron) (Wt. percent) | 10 | 10 | 13 | 10 | 13 | 15 | 15 | 15 | — | — | — |
| Choline Chloride Content of Encap- | 35 | 35 | 33 | 30 | 34 | 33 | 33 | 33 | 42 | 49 | 56 |

TABLE I-continued

Composition of Examples 17 to 27

| Example | 17 | 18 | 19 | 20 | 21 | 22 | 23 | 24 | 25 | 26 | 27 |
|---|---|---|---|---|---|---|---|---|---|---|---|
| sulate (Wt. percent) | | | | | | | | | | | |
| Effectiveness of Encapsulate, Wt. percent released (1 hour release test) | 15 | 14 | 14 | 35 | 16 | 9 | 4 | 4 | 53 | 15 | 38 |

TABLE II

Laboratory Preparation of Dry Choline Chloride Substrates with Increased Choline Chloride Content From 60 percent Dry Choline Chloride

| Example No. | 60% Dry Choline Chloride Grams | 70% Aqueous Choline Chloride, G | % Choline Chloride Calculated | % Choline Chloride By Analysis |
|---|---|---|---|---|
| 28 | 100 | 50 | 70 | 71.2 |
| 29 | 100 | 75 | 73 | 74.6 |
| 30 | 100 | 100 | 76 | 76.8 |
| 31 | 1000 | 500 | 70 | 68.4 |

TABLE III

Laboratory Preparation of Dry Choline Chloride Substrates with Increased Choline Chloride Content From 70 percent Dry Choline Chloride

| Example No. | 70% Dry Choline Chloride Grams | 70% Aqueous Choline Chloride G | % Choline Chloride Calculated | % Choline Chloride By Analysis |
|---|---|---|---|---|
| 32 | 100 | 20 | 75 | 74.8 |
| 33 | 100 | 50 | 77.5 | 77.6 |
| 34 | 100 | 70 | 80 | 81.0 |

I claim:

1. A composition of matter comprising particles suitable for introduction of a bioactive substance to the post-rumen portion of the digestive system of a ruminant substantially without introducing said substance to the rumen portion of the digestive system, said particles having a specific gravity between about 0.3 and 2.0 and comprising:
   (a) a core comprising bioactive substance;
   (b) a hydrophobic coating encapsulating said core in a quantity sufficient to essentially preclude introduction of bioactive substance into the rumen; and
   (c) a surfactant applied to the surface of the hydrophobic coating in a quantity sufficient to ensure that said particles do not float on the rumen.

2. A composition of matter according to claim 1, wherein said bioactive substance is choline chloride.

3. A composition of matter according to claim 2, wherein the choline chloride is dry choline chloride on a cereal carrier.

4. A composition of matter according to claim 3, wherein the dry choline chloride on a cereal carrier is about 60 percent by weight choline chloride.

5. A composition of matter according to claim 3, wherein the dry choline chloride on a cereal carrier is about 70 percent by weight choline chloride.

6. A composition of matter according to claim 1, wherein said hydrophobic coating comprises hydrogenated vegetable oil.

7. A composition of matter according to claim 6, wherein said hydrogenated vegetable oil is selected from the group consisting of hydrogenated palm oil, hydrogenated cottonseed oil, hydrogenated soybean oil, hydrogenated corn oil, hydrogenated peanut oil, hydrogenated palm kernel oil, hydrogenated babassu oil, hydrogenated sunflower oil, hydrogenated safflower oil, and mixtures thereof.

8. A composition of matter according to claim 7, wherein said hydrogenated vegetable oil is hydrogenated soybean oil.

9. A composition of matter according to claim 1, wherein the hydrophobic coating comprises primarily hydrogenated vegetable oil mixed with lesser amounts of wax selected from the group consisting of beeswax, petroleum wax, rice bran wax, castor wax, microcrystalline wax, and mixtures thereof.

10. A composition of matter according to claim 9, wherein the hydrogenated vegetable oil is hydrogenated soybean oil.

11. A composition of matter according to claim 10, wherein the wax is beeswax.

12. A composition of matter according to claim 1, wherein the surfactant is selected from the group consisting of polysorbate 60, polysorbate 80, propylene glycol, sodium dioctylsulfosuccinate, sodium lauryl sulfate, lactylic esters of fatty acids, polyglycerol esters of fatty acids, and mixtures thereof.

13. A composition of matter according to claim 1, wherein the particles have a specific gravity between about 1.0 and about 2.0.

14. A composition of matter comprising particles suitable for introduction of choline chloride to the post-rumen portion of the digestive system of a ruminant substantially without introducing choline chloride to the rumen portion of the digestive system, said particles having a specific gravity between about 0.3 and 2.0 and comprising:
   (a) a core comprising approximately 70 percent by weight choline chloride on a cereal carrier; and
   (b) a hydrophobic coating encapsulating said core in a quantity sufficient to essentially preclude introduction of choline chloride into the rumen.

15. A composition of matter according to claim 1, wherein the surfactant is selected from the group consisting of polysorbate 60, polysorbate 80, sodium dioctylsulfosuccinate and mixtures thereof.

16. A composition of matter according to claim 1, wherein the quantity of said hydrophobic coating ranges from about 10 percent to about 80 percent by weight based on the total weight of encapsulate.

17. A composition of matter according to claim 13, wherein the particles have a specific gravity of at least about 1.35.

* * * * *